United States Patent [19]

Davis et al.

[11] Patent Number: 5,490,521
[45] Date of Patent: Feb. 13, 1996

[54] ULTRASOUND BIOPSY NEEDLE

[75] Inventors: Richard E. Davis, Grand Rapids, Mich.; Garey L. McLellan, Henderson, Nev.

[73] Assignee: Medtronic, Inc., Minneapolis, Minn.

[21] Appl. No.: 291,342

[22] Filed: Aug. 16, 1994

Related U.S. Application Data

[63] Continuation of Ser. No. 115,155, Aug. 31, 1993, abandoned.

[51] Int. Cl.⁶ .................................................. A61B 8/12
[52] U.S. Cl. .................................................. 128/662.02
[58] Field of Search .................. 128/662.02, 662.05, 128/654, 763; 604/100, 264, 272

[56] References Cited

U.S. PATENT DOCUMENTS

| | | |
|---|---|---|
| D. 302,589 | 8/1989 | McMenamy et al. . |
| 4,058,114 | 11/1977 | Soldner . |
| 4,401,124 | 8/1983 | Guess et al. ............... 128/662.02 |
| 4,407,294 | 10/1983 | Vilkomerson . |
| 4,428,379 | 1/1984 | Robbins et al. . |
| 4,431,006 | 2/1984 | Trimmer et al. . |
| 4,493,653 | 1/1985 | Robbins et al. . |
| 4,582,061 | 4/1986 | Fry ........................... 128/662.05 |
| 4,869,259 | 9/1989 | Elkins ......................... 128/662.02 |
| 4,887,606 | 12/1989 | Yock et al. . |
| 4,977,897 | 12/1990 | Hurwitz ....................... 128/662.05 |
| 5,201,314 | 4/1983 | Bosley et al. ................ 128/662.02 |

FOREIGN PATENT DOCUMENTS 2425724  12/1975  Germany .

OTHER PUBLICATIONS

"ECHOTIP® Needles, Improved Visibility for Ultrasound," Cook Co., date unknown.
"WESTCOTT® Biopsy Needle, The Safety of Fine Needle Biopsy . . . Plus Larger Sample Size," *Becton Dickinson*, 1991.
"ULTRA–vue™ Needles, Creates an Unmistakable 'Signature' Under Ultrasound," *Becton Dickinson*, 1991.
"SampleMASTER™, *INRAD® A Division of DLP, Inc.,* " Copyright 1992.
"Ghiatas™ Beaded Breat Localization Wire," p. 15, *INRAD 1992 Product Catalog,* 1992.
"Coaxial Biopsy Needle Set, Directions for Use," *INRAD, A Division of DLP, Inc.,* Copyright 1991.

*Primary Examiner*—George Manuel
*Attorney, Agent, or Firm*—Varnum, Riddering, Schmidt & Howlett

[57] ABSTRACT

An echogenic medical needle is disclosed which comprises a tubular cannula body, a stylet received within the cannula body, and an echogenicity enhancement within the cannula for improved ultrasound imaging. Preferably, the echogenicity enhancement is on the stylet and comprises a series of annular grooves about the stylet.

23 Claims, 4 Drawing Sheets

ULTRASOUND BIOPSY NEEDLE

This is a continuation, of application Ser. No. 08/115,155 filed Aug. 31, 1993 now abandoned.

BACKGROUND OF THE INVENTION

1. Field of the Invention

This invention relates in general to medical needles, and more particularly, to medical needles having enhanced echogenicity.

2. Description of Related Art

During the past several decades, ultrasonic imaging techniques have become increasingly prevalent in clinical diagnoses, and more particularly in obstetrics, gynecology and urology. Specialists in these disciplines use reflected ultrasound wave energy to image a wide variety of medical abnormalities, including malignant and benign cysts and tumors and fetal status in utero, as well as "real-time" monitoring of needle location during such procedures as fetal blood sampling, amniocentesis, tissue aspiration biopsy and core biopsy. Considerable effort has been expended to significantly enhance the ultrasound image of a needle, or at least its point or tip, in order more accurately to pinpoint its placement during real-time ultrasonic guidance. Not only is accurate guidance required to obtain the proper sample, but it is also necessary to avoid puncture or damage to tissues.

The term echogenicity refers to the relative extent that a surface reflects incident ultrasound wave energy directly back to a sensor, which is proximal to the source or emitter of the ultrasonic wave energy. The low practical echogenicity of a smooth cannula hampers accurate imaging of the cannula within a patient's body. When the smooth cannula is oriented at right angles to the ultrasound waves, the ultrasound waves are directly reflected off the cannula back to the ultrasound transducer, and the cannula is said to have a relatively high practical echogenicity. At other orientation angles, less of the ultrasound energy is directly reflected back to the transducer reducing the practical echogenicity of the cannula.

Prior biopsy needle designs have attempted to increase the echogenicity of the cannula by presenting a roughened outer surface or diffraction grating on the cannula. However, this has the disadvantage of increasing trauma to the body tissue as the cannula is inserted, causing increased discomfort to the patient.

For instance, U.S. Pat. No. 4,401,124, issued Aug. 30, 1993 to Guess et. al., outlines some of the problems associated with monitoring the insertion and guidance of needles and other instruments using ultrasound imaging. The Guess et. al. patent also discloses a proposed solution to the monitoring problem by providing, in an ultrasound pulse-echo imaging system, a diffraction grating disposed on the surface of the surgical instrument. The diffraction grating is disclosed to have a specified distance between the depth of adjacent grooves, that distance D being a function of various parameters including the center wavelength λo of the transducer and the angle θ between the incident beam and a line along the surface of the instrument perpendicular to the grooves.

U.S. Pat. No. 4,869,259, issued Sep. 26, 1989 to Elkins, discloses a surgical instrument such as a needle which is particle blasted to produce a uniformly roughened surface portion for use with an ultrasound imaging system to provide real-time monitoring of the location of a specific portion of the needle during insertion and guidance inside the patient's body. U.S. Pat. No. 4,977,897 issued Dec. 18, 1990 to Hurwitz, teaches a similar approach where, in addition to the roughened surface portion, the needle has one or more sounding apertures formed thereon. The diameter of each sounding aperture is substantially equal to a predetermined wavelength of an incident ultrasonic wave energy beam.

Great effort has been expended to produce a biopsy needle with enhanced echogenicity; however, any protrusions or roughness on the outer surface of the cannula greatly enhances the trauma experienced by the patient during insertion of the cannula into the patient's body. One attempt to overcome this limitation or disadvantage is described in laid-open German Patent Application No. 2,425,724 in the name of Siemens AG, wherein the outer surface of the entire cannula disclosed is coated with a thin Teflon layer for reducing the puncture friction resistance of the cannula. However, the outer surface of the disclosed cannula is still quite rough due to the echogenicity enhancing ridges on its outer surface.

SUMMARY OF THE INVENTION

In its broader aspects, the invention provides an echogenic medical needle comprising a tubular cannula body having a distal end and a proximal end, a stylet received within the cannula body, and an echogenicity enhancement within the cannula.

The echogenicity enhancement can be provided on the stylet. Preferably, the echogenicity enhancement comprises either a series of annular grooves about the stylet, a helical groove about the stylet, a series of longitudinal grooves in the surface of the stylet, or a roughened surface on the stylet.

Alternatively, the echogenicity enhancement comprises a portion of the stylet having a polygonal cross section. Further, the echogenicity enhancement can comprise a length of wire coiled about the stylet.

Alternatively, the echogenicity enhancement comprises particles of reflective material bonded to the stylet. The particles can be contained within a non-reflective material contained within a reduced diameter portion of the stylet.

These and other objects, features and advantages of the invention will be apparent from the ensuing description in conjunction with the accompanying drawings.

THE DRAWINGS

Figure 13:
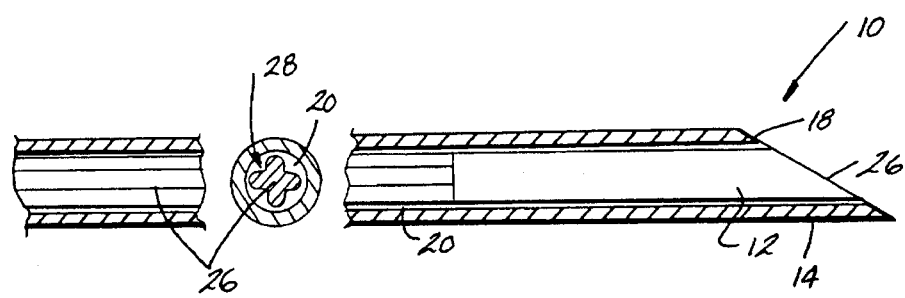
Figure 14:
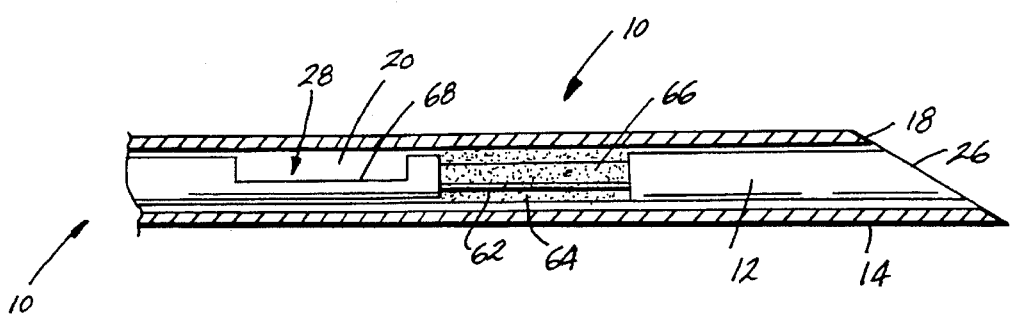

FIG. 13 is a partial sectional view of a twelfth embodiment of a medical needle according to the invention wherein the echogenicity enhancement comprises a portion of the stylet having a cruciate cross-sectional shape; and FIG. 14 is a partial sectional view of a thirteenth embodiment of a medical needle according to the invention wherein the echogenicity enhancement comprises a portion of the stylet containing a non-reflective material incorporating small particles of reflective chaff.

DESCRIPTION OF THE PREFERRED EMBODIMENTS

Figure 1:
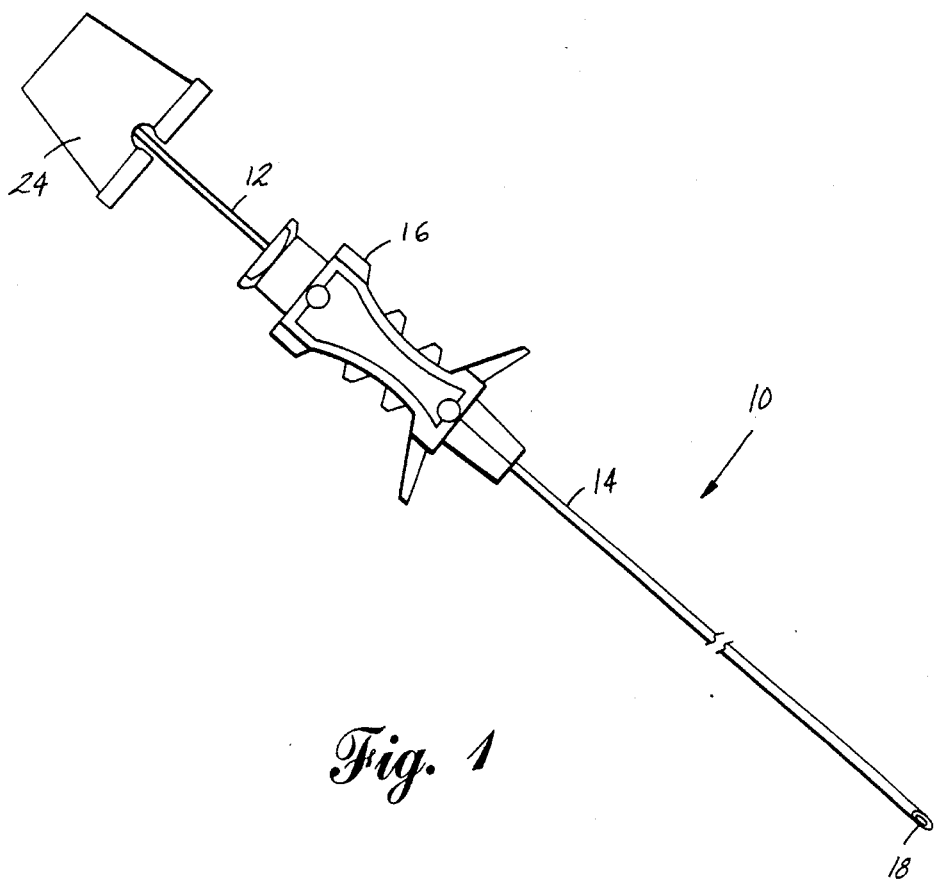
FIG. 1 illustrates a side elevational view of a medical needle according to the invention, having a stylet disposed within a tubular cannula.
Figure 2:
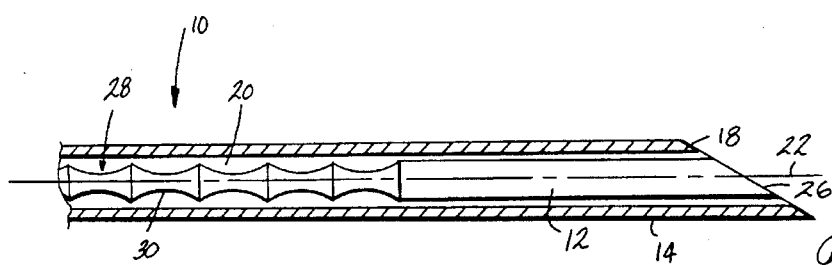
FIG. 2 is a partial sectional view of a distal tip of the medical needle of FIG. 1, illustrating an echogenicity enhancement comprising a plurality of adjacent shallow concave annular grooves about an outer surface of the stylet.

FIG. 1 illustrates a biopsy needle 10 according to the invention comprising a stylet 12 received within a narrow diameter (18 to 22 gauge) hollow cannula 14. The cannula 14 comprises a proximal hub 16, a sharp distal tip 18, and a central lumen 20 therethrough (FIG. 2). The outer surface of the cannula 14 is preferably polished to a smooth finish and formed of a material suitable for introduction into the human body such as stainless steel. To further ease the introduction of the cannula 14 into a portion of a human body, the outer surface of the cannula 14 can be coated with silicone.

As shown in FIG. 2, the biopsy needle 10 is of the Chiba style, wherein the cannula distal tip 18 is beveled at an acute angle to a longitudinal axis 22 of the cannula 14. The stylet 12, similarly comprises a proximal hub 24 (FIG. 1) and a sharp beveled distal tip 26. With the stylet 12 fully received within the cannula lumen 20, the beveled surfaces of the cannula distal tip 18 and of the stylet distal tip 26 preferably align to form a smooth cutting surface. Other tip designs commonly used in the art, such as a Franseen tip having multiple beveled surfaces, may substitute for the Chiba type tip illustrated in FIGS. 1 and 2.

In a fine-needle aspiration biopsy, a surgeon uses the biopsy needle 10 to obtain a sample of tissue cells and surrounding fluid from a specific area of a patient's body. The surgeon inserts the cannula distal tip 18, with the stylet distal tip 26 received and properly aligned within, into the patient's body in the direction of the desired area. In many procedures, ultrasound imaging using pulsed sound energy provides real-time information to the surgeon concerning the location of the cannula distal tip 18 with respect to a desired area of the patient's body.

In the present invention, the outer surface of the cannula 14 is smooth and polished to reduce tissue trauma and patient discomfort, while an echogenicity enhancement 28 on the stylet 12 within the cannula lumen 20 increases the perceived echogenicity of the biopsy needle 10 within the body. The term echogenicity refers to the relative extent that a surface reflects incident ultrasound wave energy directly back to a sensor, which is proximal to the source or emitter of the ultrasonic wave energy. Ultrasound energy from a transducer (not shown) reflects off of the echogenicity enhancement 28, through the wall of the cannula 14 and back to the transducer. As shown in FIG. 2, the echogenicity enhancement 28 comprises a portion of the stylet 12 wherein a plurality of adjacent shallow concave annular grooves 30 circumscribe the outer surface of the stylet 12. The portion of the stylet having the grooves 30 preferably approaches the stylet distal tip 26 closely, as accurate placement of the sharp distal tips of the stylet and cannula 26, 18 remains the ultimate goal of the echogenicity enhancement 28. The grooves 30 may extend proximally to the stylet hub 24 for enhanced imaging of essentially the entire biopsy needle 10, but need only be located adjacent the distal tip 26 for accurate placement thereof.

The grooves 30 can be oriented and arranged to provide a diffraction grating tuned to the frequency of the ultrasound waves according to the following formula:

$$D = N\lambda_0/2 \cos \theta$$

where D is the distance between adjacent grooves 30, N is an integer, $\lambda_0$ is a center wavelength of the ultrasound energy, and $\theta$ is the incidence angle between the direction of travel of the ultrasound waves and the cannula longitudinal axis 22.

Figure 3:
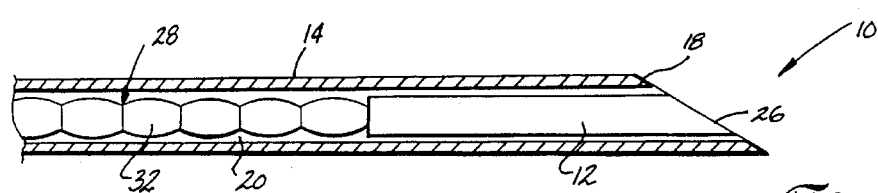
FIG. 3 is a partial sectional view of a second embodiment of a medical needle according to the invention wherein the echogenicity enhancement comprises a plurality of adjacent convex annular grooves about the stylet.
Figure 4:
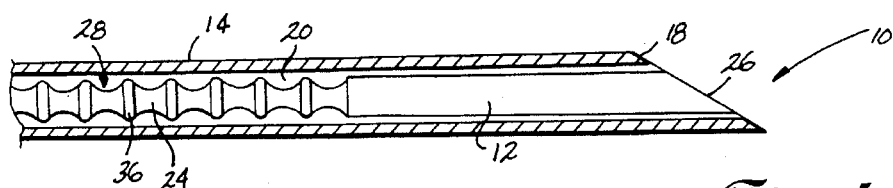
FIG. 4 is a partial sectional view of a third embodiment of a medical needle according to the invention wherein the echogenicity enhancement comprises a plurality of equally spaced apart concave annular grooves about the stylet.
Figure 5:
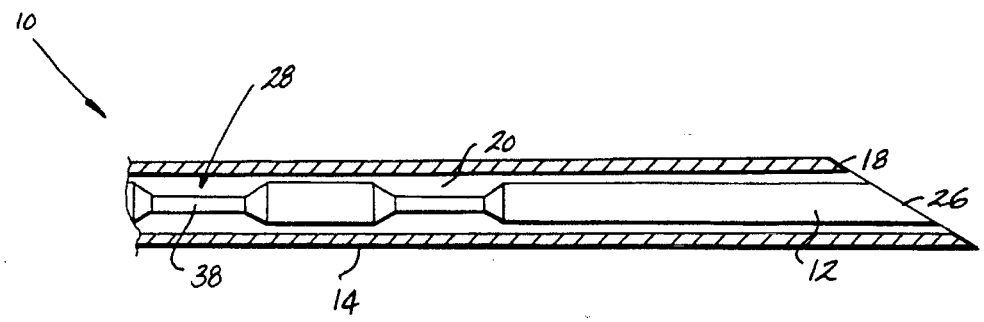
FIG. 5 is a partial sectional view of a fourth embodiment of a medical needle according to the invention wherein the echogenicity enhancement comprises a plurality of equally spaced apart truncated V-shaped annular grooves about the stylet.
Figure 6:
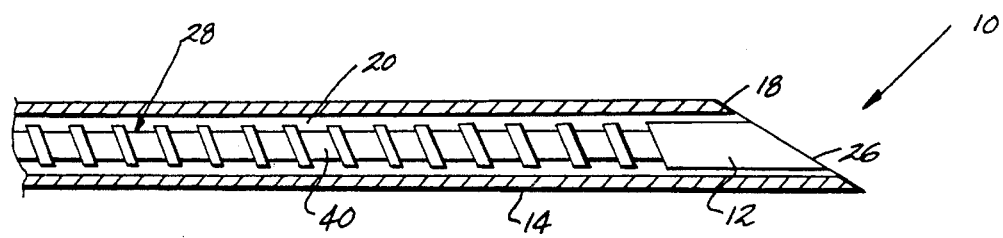
FIG. 6 is a partial sectional view of a fifth embodiment of a medical needle according to the invention wherein the echogenicity enhancement comprises a continuous spiral groove, having a square cross-sectional shape, about the stylet.

Further expedients for enhancing echogenicity of the stylet 12 are illustrated in FIGS. 3 through 14, wherein like parts are numbered with like numerals. As shown in FIG. 3, the echogenicity enhancement 28 may comprise a plurality of adjacent convex annular grooves 32 about the outer surface of the stylet 12. Alternatively, as shown in FIG. 4, the echogenicity enhancement 28 may comprise a plurality of equally spaced apart concave annular grooves 34 about the outer surface of the stylet 12, wherein intervals 36 between adjacent grooves 34 are convex. As shown in FIG. 5, the echogenicity enhancement 28 may comprise a plurality of equally spaced apart annular grooves 38 about the outer surface of the stylet 12, and wherein each groove 38 has a truncated V-shape.

Any of the grooves 30, 32, 34, or 38 previously described can be formed as a continuous spiral as opposed to separate annular grooves. For example, in FIG. 6 the echogenicity enhancement 28 comprises a continuous spiral groove 40 about the surface of the stylet 12, wherein the groove has a generally square cross sectional shape.

Figure 7:
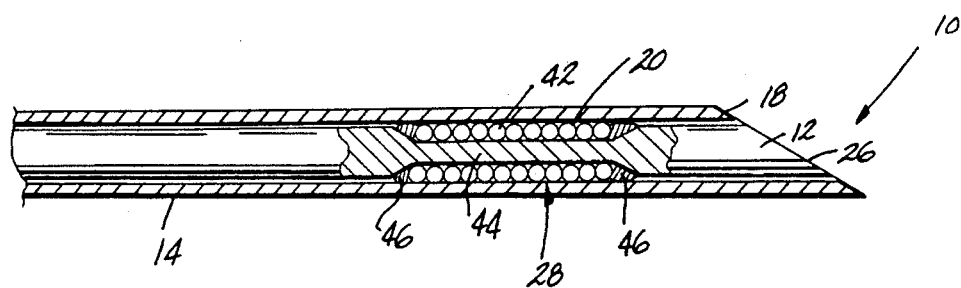
FIG. 7 is a partial sectional view of a sixth embodiment of a medical needle according to the invention wherein the echogenicity enhancement comprises a wire coiled about the stylet.
Figure 8:
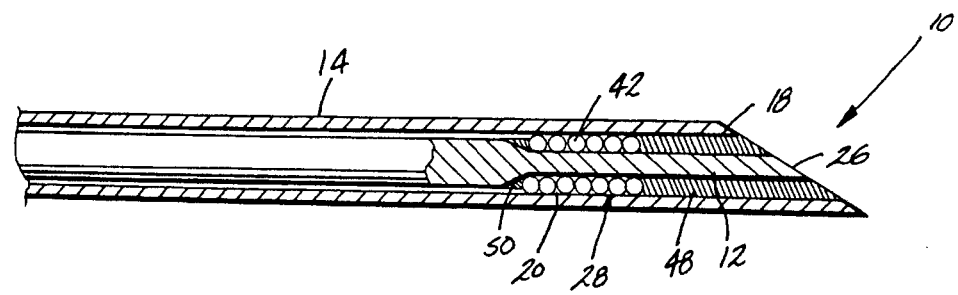
FIG. 8 is a partial sectional view of a seventh embodiment of a medical needle according to the invention wherein the echogenicity enhancement comprises a wire coiled about the stylet, and the distal tip of the stylet is partially formed of milled solder.

FIG. 7 illustrates an alternative method for forming a spiral pattern on the stylet 12. A wire coil 42 spirals about a reduced diameter portion 44 of the stylet 12, and is attached at each end of the reduced diameter portion 44 by means of solder 46. Alternatively, as shown in FIG. 8, the wire coil 42 spirals about a narrow diameter stylet 12, and solder 48 at the stylet distal tip 26 secures one end of the wire coil 42 to the stylet 12, and additional solder 50 secures the opposite end of the wire coil 42 to the stylet. The solder 48 at the distal end 26 is milled to form the beveled stylet distal tip 26 conforming to the cannula distal tip 18.

Figure 9:
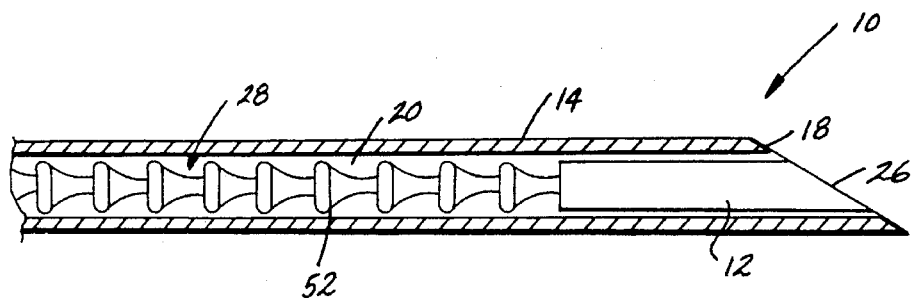
FIG. 9 is a partial sectional view of an eighth embodiment of a medical needle according to the invention wherein the echogenicity enhancement comprises a series of conical campanulate beads arranged in end-to-end relationship to form the stylet.

In FIG. 9, the stylet 12 comprises a series of conical campanulate beads 52 arranged in end to end relationship to form the elongated stylet 12.

Figure 11:
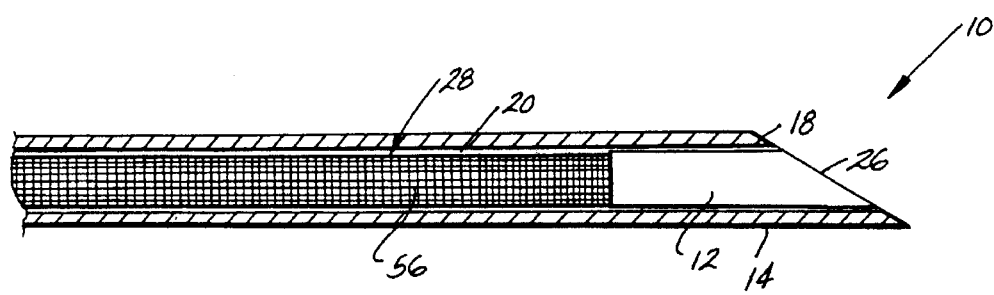
FIG. 11 is a partial sectional view of a tenth embodiment of a medical needle according to the invention wherein the echogenicity enhancement comprises a cross-hatch pattern upon the outer surface of the stylet.
Figure 10:
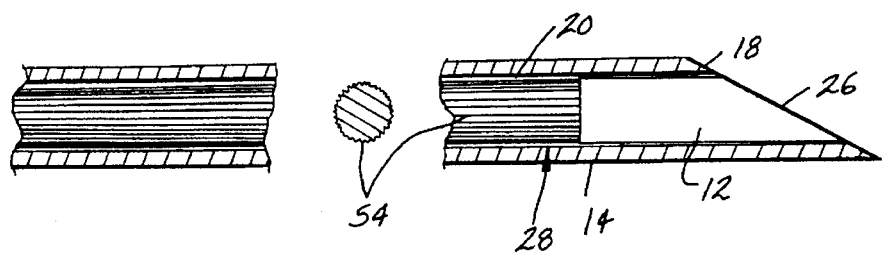
FIG. 10 is a partial sectional view of a ninth embodiment of a medical needle according to the invention wherein the echogenicity enhancement comprises a series of narrow and shallow longitudinal grooves along the surface of the stylet.

Longitudinal patterns on the stylet 12 also provide echogenicity enhancement. For instance, FIG. 10 illustrates a stylet 12 wherein the echogenicity enhancement 28 comprises a series of narrow and shallow longitudinal grooves 54 along the surface of the stylet 12, arranged in a pattern encircling the stylet 12. Alternatively, FIG. 11 illustrates the echogenicity enhancement 28 as a cross-hatched pattern 56. Alternative roughened sections similar to the cross hatched pattern 56, such as a particle blasted section (not shown) can also provide echogenicity enhancement 28.

Figure 12:
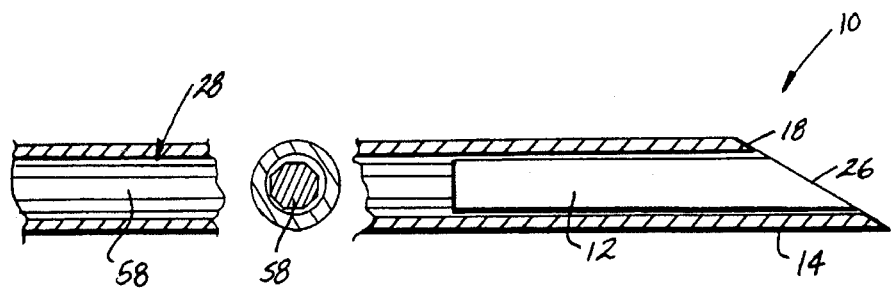
FIG. 12 is a partial sectional view of an eleventh embodiment of a medical needle according to the invention wherein the echogenicity enhancement comprises a portion of the stylet having a hexagonal cross-sectional shape.

Further, the longitudinally oriented echogenicity enhancement 28 can comprise an elongated section of the stylet 12 having various cross sectional shapes. For example, FIG. 12 illustrates such a section 58 wherein the cross sectional shape is hexagonal, whereas FIG. 13 illustrates such a section 60 wherein the cross sectional shape is cruciate.

As an alternative to forming an echogenicity enhancing pattern upon the stylet 12, FIG. 14 illustrates the echogenicity enhancement 28 as a reduced diameter section 62 of the stylet 12 filled with epoxy 64 or similar material containing small particles of plastic or metal "chaff" 66 of a sound reflecting nature. For purposes of illustration, the stylet 12 of FIG. 14 is illustrated with a sample notch 68, to show that all types of cutting stylets may be echogenically enhanced according to the present invention.

While particular embodiments of the invention have been shown, it will be understood, of course, that the invention is not limited thereto since modifications can be made by those skilled in the art, particularly in light of the foregoing teachings. Reasonable variation and modification are possible within the foregoing disclosure of the invention without departing from its true spirit and scope. For instance, the echogenicity enhancement 28 may be provided upon the inner surface of the cannula 14, particularly on the inner wall of the lumen 20, thus providing enhanced echogenicity while retaining a smooth outer surface to the cannula 14. The invention is particularly described in connection with certain specific embodiments thereof by way of illustration and not of limitation, and the scope of the appended claims should be construed as broadly as the prior art will permit.

What is claimed is:

1. An echogenic medical needle comprising a tubular cannula body having a distal end and a proximal end, a stylet having a distal end and a proximal end, the stylet being received within the cannula body, and an echogenicity enhancement formed on one of the stylet and cannula body intermediate the proximal and distal ends thereof, the echogenicity enhancement comprising an annular series of contoured elements immediately adjacent one another and repetitively provided on said one of the stylet and cannula body and a series of longitudinal grooves in the surface said one of the stylet and cannula body, the contoured elements being adapted to reflect ultrasonic waves at a characteristic different from the other of the stylet and cannula.

2. An echogenic medical needle according to claim 1 wherein the echogenicity enhancement is provided on the stylet.

3. An echogenic medical needle according to claim 2 wherein the echogenicity enhancement comprises a series of annular grooves about the stylet.

4. An echogenic medical needle according to claim 2 wherein the echogenicity enhancement further comprises a plurality of flat surfaces provided on and extending longitudinally along a portion of the stylet such that said portion of the stylet is polygonal in cross section.

5. An echogenic medical needle according to claim 2 wherein the echogenicity enhancement further comprises a roughened, cross hatched surface provided on at least a portion of the stylet.

6. An echogenic medical needle according to claim 2 wherein the echogenicity enhancement comprises particles of reflective material bonded to the stylet.

7. An echogenic medical needle according to claim 1 wherein the echogenicity enhancement comprises a length of coiled wire provided on one of the stylet and the catheter body.

8. An echogenic medical needle according to claim 7 wherein the length of coiled wire is provided on the stylet.

9. An echogenic medical needle comprising:
 a tubular cannula body having a proximal end, a distal cutting end, and a smooth outer surface; and
 an elongated stylet receivable within the cannula body, the stylet having a proximal end and a distal cutting end, the distal cutting end of the stylet conforming to the distal cutting end of the cannula to form a cutting surface; and
 an echogenicity enhancement within the cannula whereby the echogenicity enhancement is readable by an imaging device using reflected wave energy, the echogenicity enhancement comprising a plurality of annular convex grooves immediately adjacent one another and repetitively provided on the stylet, the grooves being adapted to reflect ultrasonic waves at a characteristic different from the cannula.

10. An echogenic medical needle according to claim 9 wherein the echogenicity enhancement further comprises a series of longitudinal grooves in the surface of the stylet.

11. An echogenic medical needle according to claim 9 wherein the echogenicity enhancement further comprises a length of coiled wire provided on one of the stylet and the cannula body.

12. An echogenic medical needle according to claim 11 wherein the length of coiled wire is provided on the stylet.

13. An echogenic medical needle according to claim 9 and further comprising a plurality of concave grooves provided intermediate the convex grooves and the concave and convex grooves being adapted to be readable by an imaging device using reflected wave energy.

14. An echogenic medical needle according to claim 9 and further comprising a plurality of truncated cone-shaped grooves provided intermediate the convex grooves, the truncated cone-shaped and convex grooves being adapted to be readable by an imaging device using reflected wave energy.

15. An echogenic medical needle comprising a tubular cannula body having a distal end and a proximal end, a stylet having a .distal end and a proximal end, the stylet being received within the cannula body, and an echogenicity enhancement formed on one of the stylet and cannula body intermediate the proximal and distal ends thereof, the echogenicity enhancement comprising a plurality of longitudinally extending surfaces provided on at least a portion of said one of the cannula body and stylet so that said portion is-polygonal in cross section, the longitudinally extending surfaces being adapted to reflect wave energy in a characteristic differently from the other of the stylet and cannula body.

16. An echogenic medical needle according to claim 15 wherein the echogenicity enhancement is provided on the stylet.

17. An echogenic medical needle according to claim 15 wherein the echogenicity enhancement comprises a plurality of longitudinally extending grooves provided on at least a portion of the stylet.

18. An echogenic medical needle according to claim 15 wherein said portion of the stylet is hexagonal in cross section.

19. An echogenic medical needle according to claim 15 wherein said portion of the stylet is cruciate in cross section.

20. An echogenic medical needle comprising a tubular cannula body having a distal end and a proximal end, a stylet having a distal end and a proximal end, the stylet being received within the cannula body, and an echogenicity enhancement formed on one of the stylet and cannula body intermediate the proximal and distal ends thereof, the echogenicity enhancement comprising an annular series of contoured elements immediately adjacent one another and repetitively provided on said one of the stylet and cannula body and a roughened, cross hatched surface provided on at least a portion of said one of the stylet, the contoured elements being adapted to reflect ultrasonic waves at a characteristic different from the other of the stylet and cannula.

21. An echogenic medical needle comprising a tubular cannula body having a distal end and a proximal end, a stylet having a distal end and a proximal end, the styler being received within the cannula body, and an echogenicity enhancement formed on one of the stylet and cannula body intermediate the proximal and distal ends thereof, the echogenicity enhancement comprising an annular series of contoured elements immediately adjacent one another and repetitively provided on said one of the stylet and cannula body and a length of coiled wire provided on one of the stylet and the catheter body, the contoured elements being adapted to reflect ultrasonic waves at a characteristic different from the other of the stylet and cannula.

22. An echogenic medical needle comprising a tubular cannula body having a distal end and a proximal end, a stylet having a distal end and a proximal end, the stylet being received within the cannula body, and an echogenicity enhancement formed on one of the stylet and cannula body intermediate the proximal and distal ends thereof, the echogenicity enhancement comprising an annular series of contoured elements immediately adjacent one another and repetitively provided on said one of the stylet and cannula body and particles of reflective material bonded to the stylet, the contoured elements being adapted to reflect ultrasonic waves at a characteristic different from the other of the stylet and cannula.

23. An echogenic medical needle according to claim 22 further comprising a reduced diameter portion of the stylet filled with a relatively non-reflective material containing the particles of reflective material.

* * * * *

UNITED STATES PATENT AND TRADEMARK OFFICE
CERTIFICATE OF CORRECTION

PATENT NO. : 5,490,521
DATED : February 13, 1996
INVENTOR(S) : RICHARD E. DAVIS and GAREY L. McLELLAN It is certified that error appears in the above-indentified patent and that said Letters Patent is hereby corrected as shown below:

Claim 15, column 7, line 4, "is-polygonal" should read --is polygonal--.

Claim 21, column 8, line 3, "styler" should read --stylet--.

Signed and Sealed this

Tenth Day of September, 1996

Attest:

BRUCE LEHMAN

*Attesting Officer*     *Commissioner of Patents and Trademarks*